(12) United States Patent
Heinlein et al.

(10) Patent No.: US 9,119,587 B2
(45) Date of Patent: Sep. 1, 2015

(54) METHOD AND APPARATUS FOR IMPROVED DISPLAY OF DIGITAL MAMMOGRAPHIC IMAGES

(75) Inventors: Peter Heinlein, München (DE); Wilfried Schneider, Wittenbeck (DE); Marco Blumenthal, Jena (DE); Jörg Teubl, Graz (AT)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 1831 days.

(21) Appl. No.: 12/276,409

(22) Filed: Nov. 23, 2008

(65) Prior Publication Data

US 2009/0174727 A1    Jul. 9, 2009

(30) Foreign Application Priority Data

Nov. 23, 2007   (DE) .......................... 10 2007 057 014

(51) Int. Cl.
*A61B 6/00*     (2006.01)
*G06T 5/00*     (2006.01)

(52) U.S. Cl.
CPC ................. *A61B 6/461* (2013.01); *G06T 5/008* (2013.01); *A61B 6/502* (2013.01); *G06T 2207/10116* (2013.01); *G06T 2207/30068* (2013.01)

(58) Field of Classification Search
None
See application file for complete search history.

(56) References Cited

U.S. PATENT DOCUMENTS 6,961,066 B2 *  11/2005  James .......................... 345/589
7,593,561 B2 *   9/2009  Zhang et al. .................. 382/130

* cited by examiner

*Primary Examiner* — Antonio A Caschera
(74) *Attorney, Agent, or Firm* — Fletcher Yoder, P.C.

(57) ABSTRACT

A method and apparatus for the improved display of digital mammographic images, which were measured in the context of a mammographic imaging system and displayed on a workstation monitor. The mammogram consists of a plurality of pixels with each pixel having a pixel value assigned thereto. The pixel values of all pixels of the mammogram lie within a pre-determined first range of values and the pixel values of pixels of a subsection of the mammogram lie within a second range of values, which represents a subset of the first range of values. A mammogram having a subsection with increased contrast, such that the second range of pixel values of the pixels in the subsection are spread by a spreading function, whereby the amount of the spreading function changes over the subsection. In this way, an improved display is created, by means of those representations of the mammogram regarding their contrast in subsections being optimized, at the same time the representation for a user is improved without artifacts.

7 Claims, 9 Drawing Sheets

METHOD AND APPARATUS FOR IMPROVED DISPLAY OF DIGITAL MAMMOGRAPHIC IMAGES

CROSS-REFERENCE TO RELATED APPLICATIONS

This application claims the benefit of a priority under 35 U.S.C. 119(a)-(d) to German Patent Application No. 102007057014.9, filed Nov. 23, 2007, the entire contents of which are hereby incorporated by reference.

BACKGROUND OF THE INVENTION

This disclosure relates generally to a method and apparatus for improved display of digital mammographic images.

Digital mammographic images or mammograms are usually presented as gray scale images having individual pixels, with each pixel having a pixel value corresponding to a specific gray scale value. These gray scale values may lie within a range of values between a minimum value of, for example, 0 (black) and a maximum value of, for example, 225 (white). The edge length of a typical mammogram is approximately 2000 to 4000 pixels, and the dissolution of a typical mammogram is approximately 10 line pairs/mm and/or 0.1 mm/pixel.

A mammographic imaging system may be coupled to a workstation, for example, a PACS (Picture Archiving and Communication System) workstation, on which a mammogram may be viewed and reviewed by a physician or other medical professional. Mammography assigned PACS workstations usually have high resolution monitors, which are able to represent the high volume range and the comparatively high resolution of mammographic images.

Mammographic imaging systems generate raw mammograms containing measured data. These raw mammograms exhibit a global image characteristics with a comparatively high contrast in a boundary region of the measured object (i.e., the boundary region of the breast) and a relatively low contrast inside the measured object (i.e., the inside the breast). Conventional PACS workstations typically include tools for selecting parts of the whole gray scale level range and displaying these parts with maximum contrast through window level settings. Gray scale level ranges outside of the selected gray scale level window are mapped to the smallest or highest possible gray scale level, which means that information contained in these outside ranges is no longer displayed. Alternatively, nonlinear transfer functions represented through so called lookup tables may be applied to the raw mammogram modifying the global image characteristics in order to achieve a better over-all-contrast. Since the available total range of gray scale levels is fixed, a contrast enhancement for a selected part of the gray scale level range leads to a decrease of contrast in other gray level ranges. Therefore, an optimal display of all gray scale levels of the mammogram with optimal contrast and sharpness cannot be achieved by applying window level settings and/or lookup tables.

In the case of a mammogram a fundamental problem results in the fact that it is difficult to visualize structures within the breast. At the same time, structures within the background do not have to be visualized. The actual interesting structures are represented within the breast by pixel values, which do not use the entire range of values available, but use values within a comparatively small range. Therefore, the contrast between the pixels of the actual interesting structures is thus comparatively small.

Well known level and window functions use a global adjustment of the contrast between the pixels for contrast optimization, as for example the contrast between pixels with pixel values in a certain range of values is increased (the range of values is spread), all pixels with pixel values outside of this range of values however on the minimum or maximum pixel value is at the same time are set In this way, the contrast for certain structures, for example within the represented close gland fabric of a breast may be optimized, while the contrast within other ranges, received at the same time, are not optimal and may be within set ranges, so that the information is not represented into individual ranges any longer.

Therefore, there is a need for a method and apparatus for an intuitive way for a physician or other medical professional to locally optimize the contrast of a mammographic image in a particular portion of the mammographic image.

BRIEF DESCRIPTION OF THE INVENTION

In accordance with an aspect of the disclosure, a
In accordance with an aspect of the disclosure, a
In accordance with an aspect of the disclosure, a system
In accordance with an aspect of the disclosure, a method
Various other features, aspects, and advantages will be made apparent to those skilled in the art from the accompanying drawings and detailed description thereof.

DETAILED DESCRIPTION OF THE INVENTION

Figure 1:
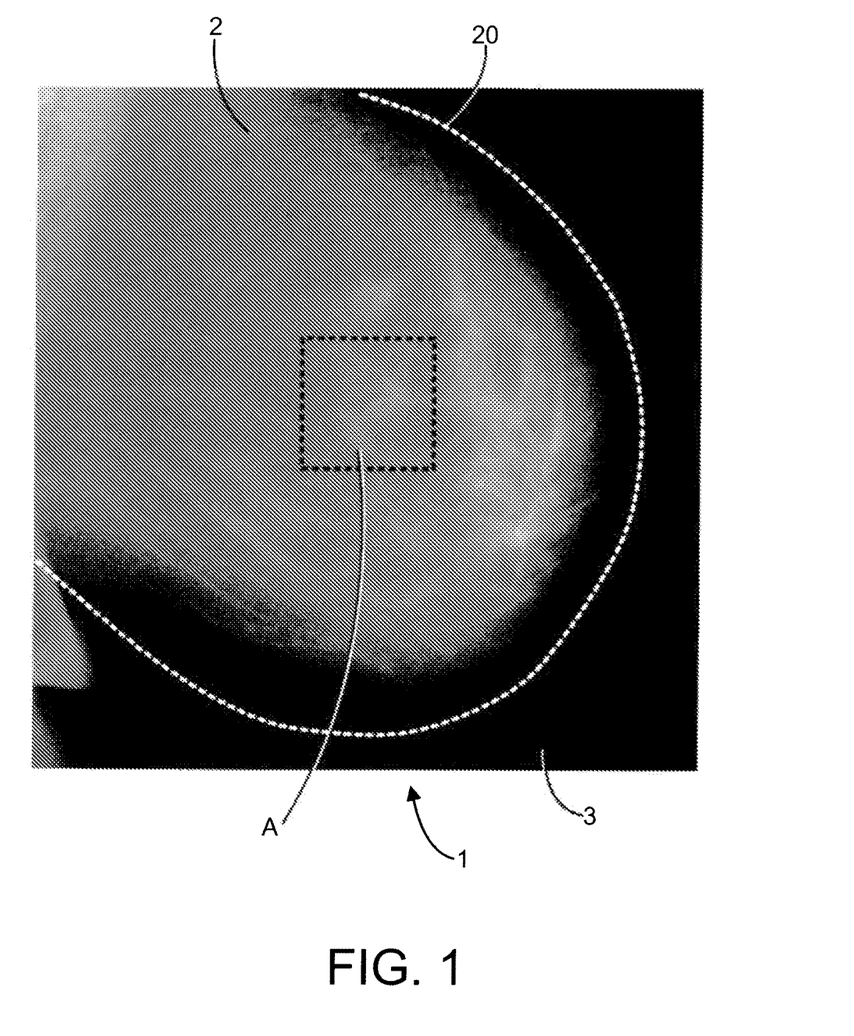
FIG. 1 is a digital mammogram.

Referring now to the drawings, FIG. 1 illustrates a digital mammogram 1, which represents measured data in the context of a mammography investigation. The measured data is composed of a plurality of pixels having a variety of pixel values. The digital mammogram 1 may have been obtained directly from a digital mammography system having a digital detector or obtained from an analog mammography system where the image is later digitized. For example, direct digital platforms, digitized film platforms, and computed radiography (CR) film platforms. In the mammogram 1 an image of the breast 2 is represented, which stands out from a dark background 3. The breast image 2 is separated from the background 3 by an outline line 20. FIG. 1 also shows a cutout A within the breast image of the mammogram 1.

The mammogram 1 may exhibit, for example, edge lengths of 4000+5500 pixels, whereby a gray scale pixel value is assigned to the individual pixels in each case. The pixel values of the individual pixels lie within a pre-determined range. The structure of the breast 2 is represented most brightly by a minimum value (e.g., 0 (black)), according to the black background 3, up to a maximum value (e.g. 255 (white)). The range of values is available for use by a display monitor, which is limited for representation to a finite range by discretely represented pixel values (e.g. gray scale values).

It is clearly evident in the mammogram 1 that the contrast between the breast 2 and the background 3 is large. However, the contrast between the different structures within the breast 2 are comparatively small.

Figure 2:
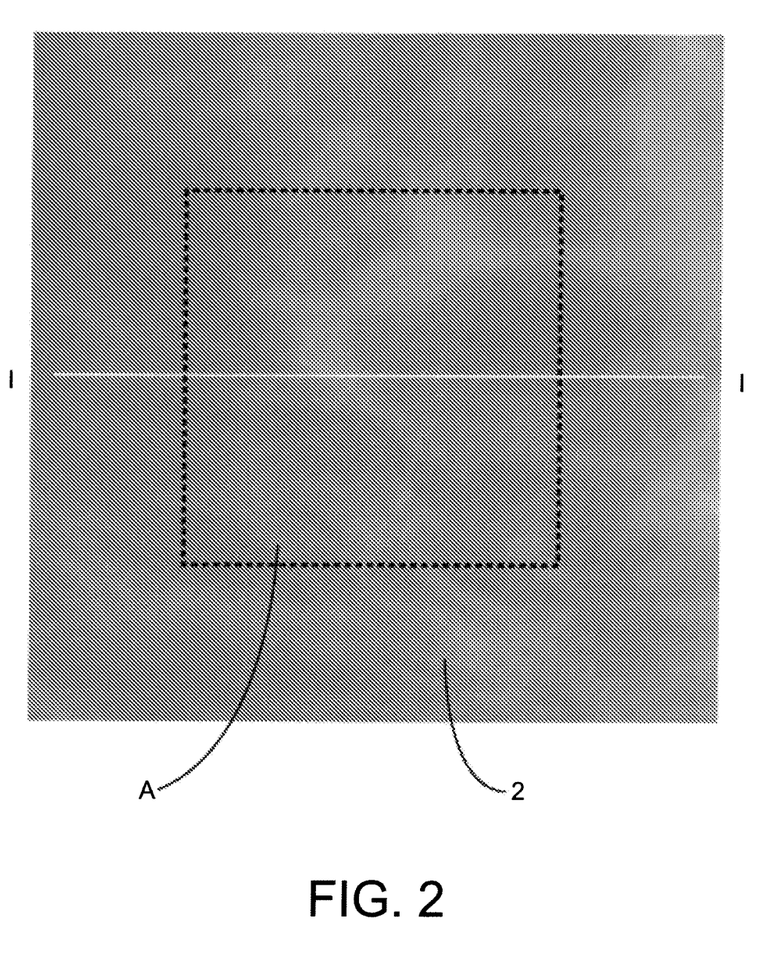
FIG. 2 is an enlarged portion of the digital mammogram of FIG. 1.

FIG. 2 shows an enlarged image of a cutout A within the mammogram 1. This image clarifies that the contrast of the structures within the breast 2 is low, making it difficult to recognize different structures within the breast 2 for a viewer.

Figure 3:
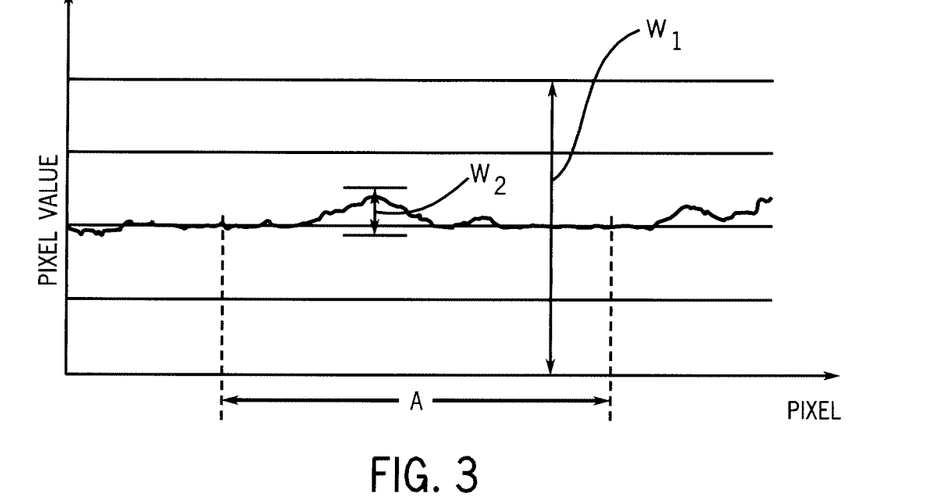
FIG. 3 is a graphical representation of the pixel values of the digital mammogram along line I-I of FIG. 2.

FIG. 3 illustrates a graphical representation of the pixel values of the digital mammogram 1 along line I-I of FIG. 2. The pixel values of a mammogram lie within a global pre-determined range of values W1, which is clearly larger than the range of values W2, with which the pixels in the cutout A inside the breast 2 are represented. This is due to the fact that the large range of values W1 include both the pixels in the black background 3 and the pixels within the bright (white) structures of the breast 2. Thus only a relatively small range of values, in the cutout A according to the range of values W2 for the structures within the breast 2, remain within the pixel values of pixels that lie inside the breast 2, so that the pixels exhibit a relatively small contrast to each other inside the breast 2. Therefore, the structures of the breast 2 are not represented to a viewer with optimal contrast.

Figure 4:
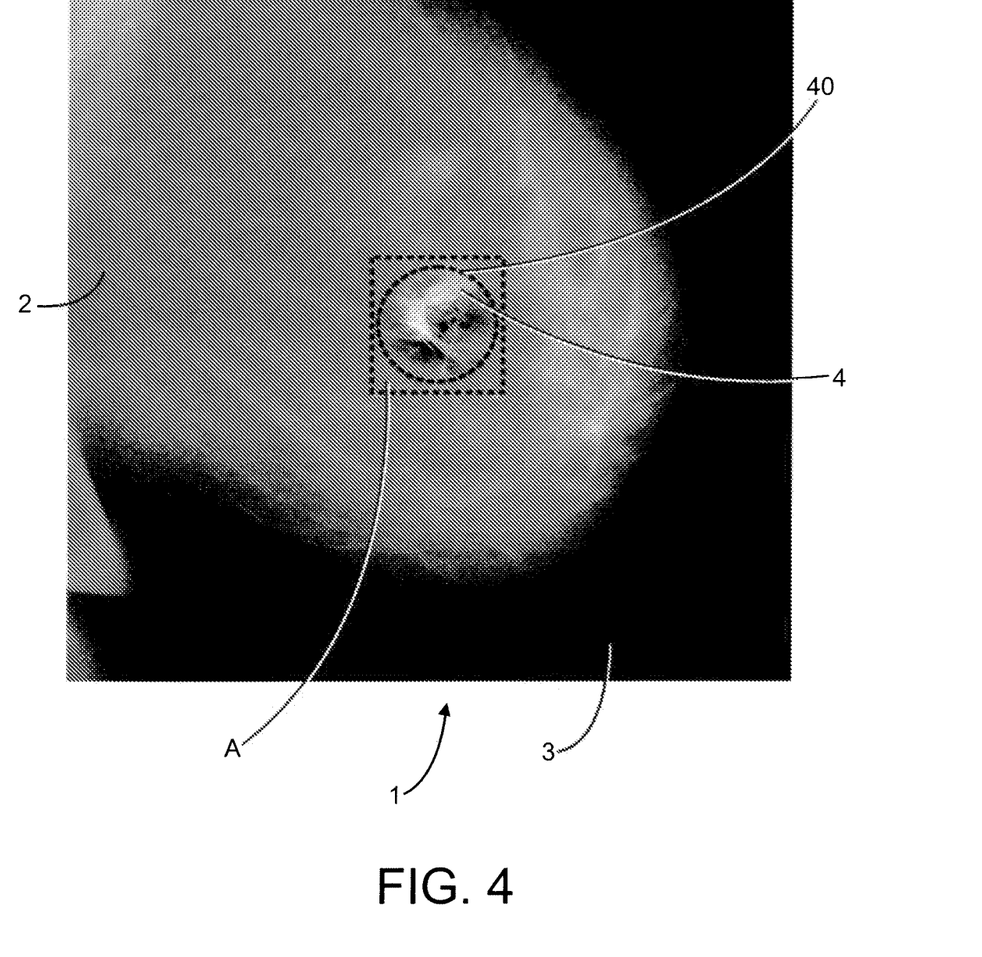
FIG. 4 is a digital mammogram exhibiting a subsection with increased contrast.

FIG. 4 illustrates a digital mammogram 1 exhibiting a subsection 4 with increased contrast. The contrast between the pixel values of the pixels is increased locally. In FIG. 4, the represented mammogram 1 includes a cutout A and a subsection 4 having a circular outline 40 within the cutout A. The contrast of the image within the subsection 4 is optimized by expanding the pixel value of the pixels within the subsection 4 with a spreading function. The pixel values of the pixels in subsection 4 use an increased range of values, and thus exhibit an increased contrast. The spreading function is used for expanding the pixel value range in subsection 4 to the maximum available range for optimal contrast.

Figure 5:
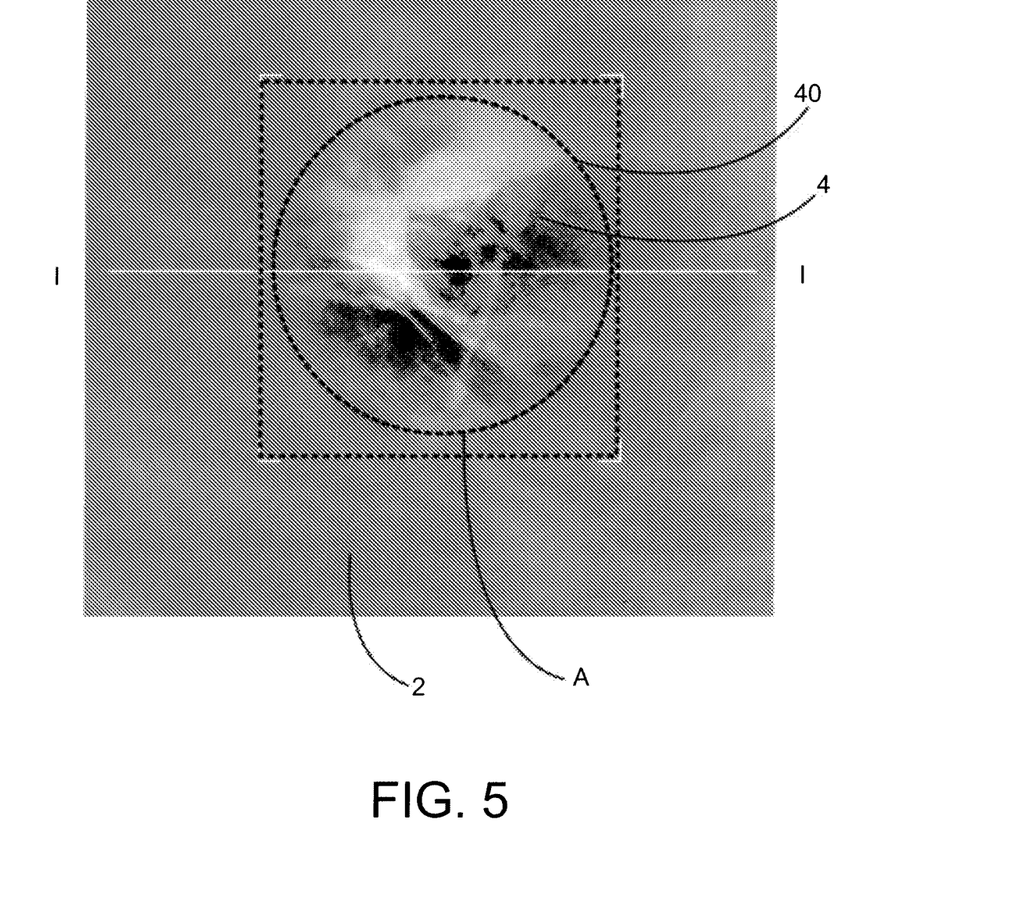
FIG. 5 is an enlarged portion of the digital mammogram of FIG. 4.

FIG. 5 illustrates an enlarged portion of the digital mammogram 1 of FIG. 4. FIG. 5 shows an enlarged image of the cutout A and subsection 4 within the mammogram 1. This image clarifies that the contrast of the structures within the subsection 4 is increased.

Figure 6:
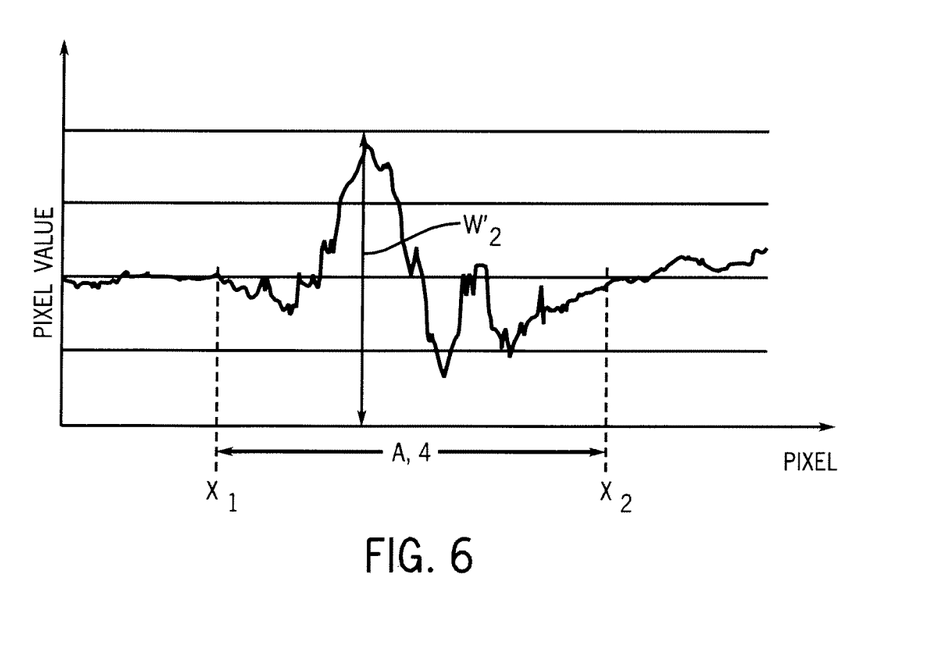
FIG. 6 is a graphical representation of the pixel values of the digital mammogram along line I-I of FIG. 5.

FIG. 6 illustrates a graphical representation of the pixel values of the digital mammogram 1 along line I-I of FIG. 5. In FIG. 6, the pixel values along the line I-I of FIG. 5 are represented. It is evident that the range of pixel values W2' within subsection 4 was spread or increased, and limited by the pixels X1, X2. The spread range of pixel values W2' may correspond to a maximum representation of mammogram 1 with the available range of values W1, so that the pixel values use the largest range of values W1 that are available within the subsection 4 and thus between the smallest arising pixel value and the largest arising pixel value yielding maximum contrast results. Is clearly evident in FIGS. 4 and 5 that the smallest pixel value accepts the minimum value (black), during which largest pixel value accepts the maximum value (white) it exhibits.

As shown in FIGS. 4 and 5, subsection 4 exhibits pixel values with an optimized contrast. The circular outline 40 provides a boundary to subsection 4. In order to prevent artifacts in the boundary of subsection 4 a variable weighting function is used for spreading the pixel values over the subsection 4, where the amount of weighting function decreases near the boundary of the subsection 4, so that a soft transition occurs between the subsection 4 and the original mammogram 1. The weighting function is used for decreasing contrast optimization towards the boundary of subsection 4.

Figure 7:
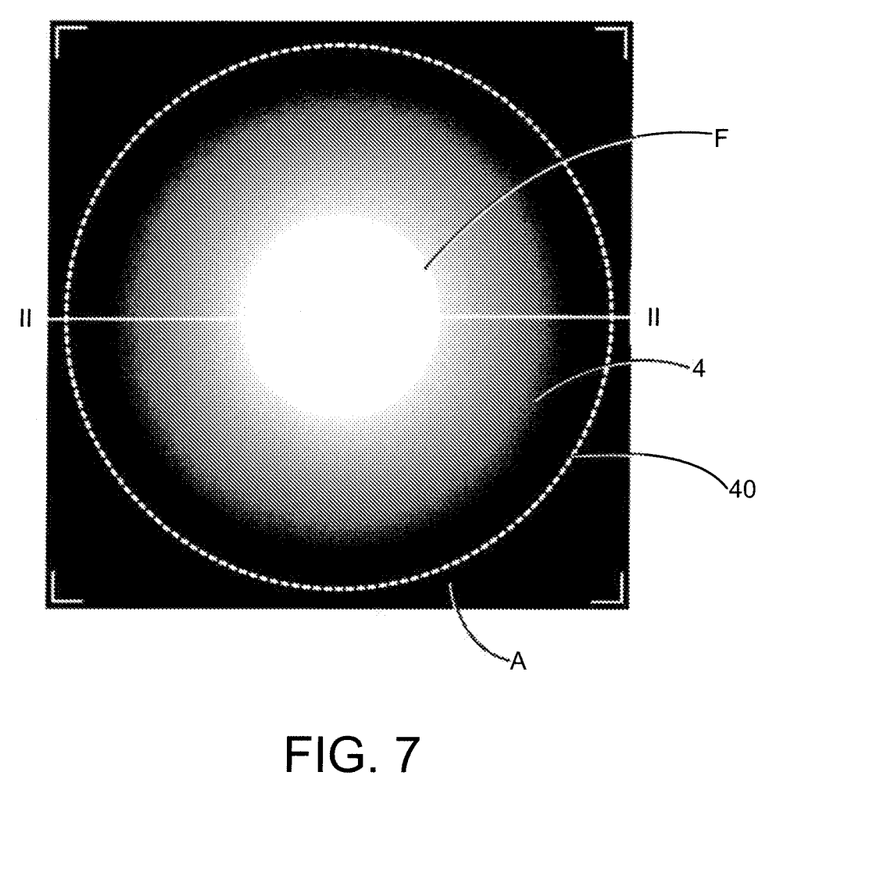
FIG. 7 is a gray scale pixel value figurative representation of a weighting function.

FIG. 7 illustrates a gray scale pixel value figurative representation of a weighting function F. In FIG. 7, the weighting function F used is illustrated in a gray scale value representation. The weighting function is rotationally symmetric and exhibits a circular outline 40. From the outline 40 of the subsection 4, the amount of weighting function F increases from the outline 40 and rises to a maximum value at the center of the subsection 4. The weighting function F exhibits a maximum value of 1 (white) at the center.

Figure 8A:
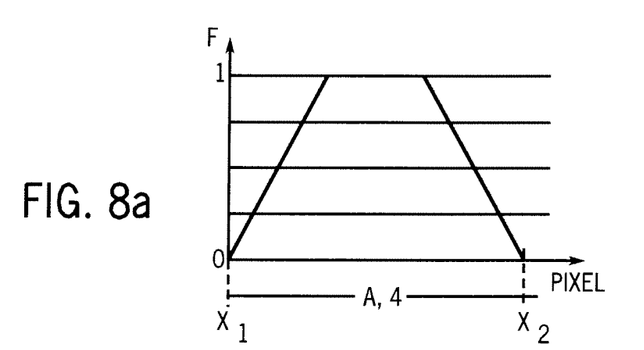
FIG. 8a is a graphical representation of the amount of the weighting function along the line II-II of FIG. 7.

FIG. 8*a* illustrates a graphical representation of the amount of the weighting function F along the line II-II of FIG. 7. In this example, the weighting function F exhibits a tapered form, where the amount of the weighting function F at the edge of the subsection 4 rises in a linear function at the pixel X1 (ramp shaped), exhibits a value of one inside subsection 4, then decreases in a linear function to pixel X2 at the edge of the subsection 4.

Figure 8B:
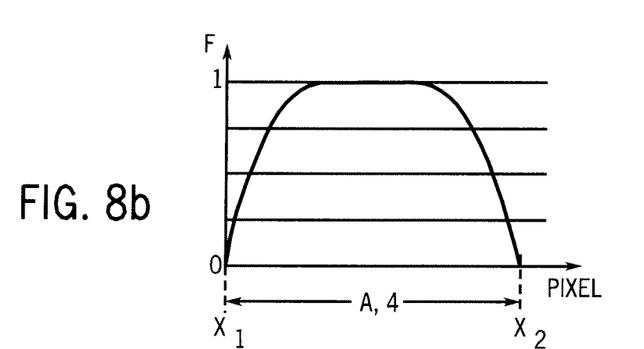
FIGS. 8b - 8c are graphical representations of the amount of other weighting functions along the line II-II of FIG. 7.
Figure 8C:
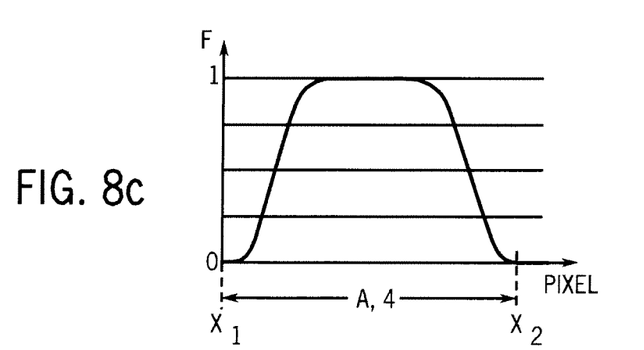

FIGS. 8*b* and 8*c* illustrate graphical representations of the amount of other weighting functions along the line II-II of FIG. 7. The weighting functions F shown in FIGS. 8*b* and 8*c* provide a softer transition at the edge of subsection 4. They both exhibit curved functions rather than the linear function of FIG. 8*a*.

The new resulting pixel values of gray scale values within the subsection 4 of the mammogram 1 are determined by the following equation:

$$g_{res} = g_{neu} \cdot F + (1-F) \cdot g_{alt} \quad \text{Equation (1)}$$

where $g_{res}$ is the pixel value (gray scale value) of the contrast optimized mammogram;

where $g_{alt}$ is the pixel value (gray scale value) before contrast optimization, according to the pixel value of the original mammogram;

where $g_{neu}$ is the pixel value (gray scale value) after contrast optimization; and where F is the weighting function with values between 0 and 1.

The computation of $g_{neu}$ depends on the selected contrast optimization function. If one selects a linear contrast spreading function, then $g_{neu}$ is determined by the following equation:

$$g_{neu} = \min + \frac{(g_{alt} - g_{min}) \cdot (\max - \min)}{(g_{max} - g_{min})} \quad \text{Equation (2)}$$

where $g_{alt}$ is the pixel value (gray scale value) before contrast optimization, according to the pixel value of the original mammogram;

where $g_{neu}$ is the pixel value (gray scale value) after contrast optimization;

where min is the smallest possible pixel value (gray scale value) within the available range of values W1;

where max is the greatest possible pixel value (gray scale value) within the available range of values W1;

where $g_{min}$ is the smallest actual pixel value (gray scale value), arising in the original image of subsection 4, according to the minimum pixel value of the range of values W2; and where $g_{max}$ is the largest actual pixel value (gray scale value), arising in the original image of subsection 4, according to the maximum pixel value of the range of values W2.

Alternatively, a histogram balance function may be used for contrast optimization. In this case, $g_{neu}$ is determined by the following equation:

$$g_{neu} = \min + (\max - \min) \cdot \frac{\sum_{g=\min}^{g_{alt}} p(g)}{\sum_{g=\min}^{\max} p(g)} \quad \text{Equation (3)}$$

where $g_{alt}$ is the pixel value (gray scale value) before contrast optimization, according to the pixel value of the original mammogram;

where $g_{neu}$ is the pixel value (gray scale value) after contrast optimization;

where min is the smallest possible pixel value (gray scale value) within the available range of values W1;

where max is the greatest possible pixel value (gray scale value) within the available range of values W1; and where p(g) is the absolute frequency of the gray scale value g in the original image (to read off from histogram).

In principle there are numerous other alternative procedures or functions for improving the contrast of only a portion or subsection of a mammographic image.

From equation (1) it follows that within the range and within which the weighting function F takes the value 1, only the pixel values $g_{neu}$ with optimized contrast are represented. The term (1-F) in the equation becomes 0 and $g_{res} = g_{neu}$). In the transition area at the edge of the subsection 4, the pixel values a $g_{neu}$ are valid as both the new contrast optimized pixel values $g_{neu}$ and resulting in pixel values in a weighted way. In the contrast optimized mammogram 1 of FIGS. 4 and 5, the represented pixel value of $g_{res}$ is received.

The weighting function F takes values between 0 and 1 and may exhibit functions as shown in FIG. 7 and FIGS. 8a to 8c.

Expanding the range of values W2 on the basis of the weighting function F in the subsection 4 results as follows:

$$W2' = W1 \cdot F + (1-F) \cdot W2 \quad \text{Equation (4)}$$

Maximum spreading corresponds to the range of values W1 (limited by the minimum pixel value min and the maximum pixel value max), so that the contrast attainable between the minimum pixel value and the maximum pixel value corresponds to the maximum range of values W1.

Figure 9:
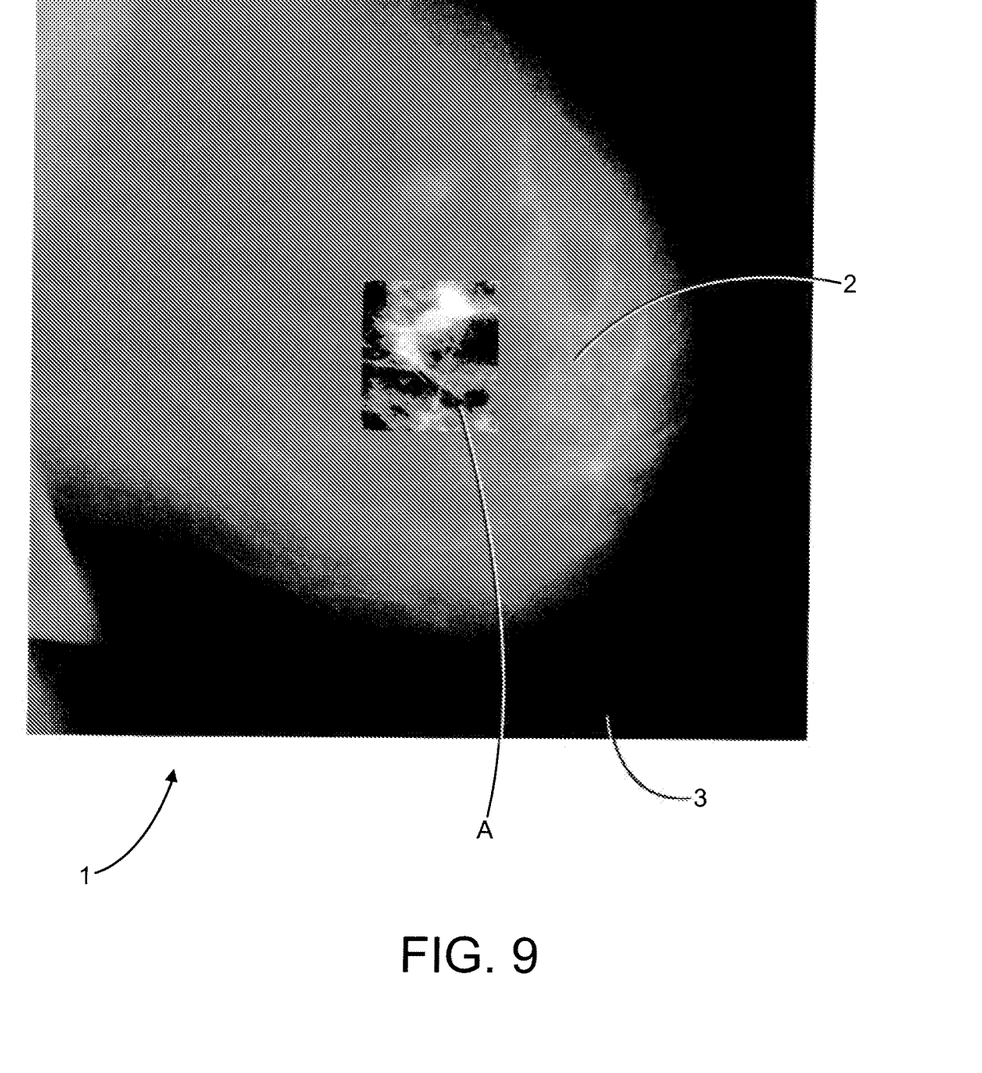
FIG. 9 is a digital mammogram exhibiting a cutout with increased contrast; a subsection the contrast between the pixel values of the pixels is increased locally; a subsection the contrast between the pixel values of the pixels on the basis a weighting function constant in the amount is locally increased.

FIG. 9 illustrates a digital mammogram 1 exhibiting a cutout A with increased contrast. The contrast between the pixel values of the pixels on the basis of a constant weighting function is locally increased. FIG. 9 shows a mammogram 1 with a cutout A. The pixel values are contrast optimized, however not in a weighted way with the original mammogram 1 overlaid. The weighting function amount is 1 and constant over cutout A. This causes sharp edges to arise in the resulting mammogram 1, which is unpleasant for the reviewing physician and may provide artifacts, because of the sharp transition between the original mammogram 1 and the contrast-optimized mammogram within cutout A. Because of this, structures in the boundary region may not be recognizable.

Figure 10:
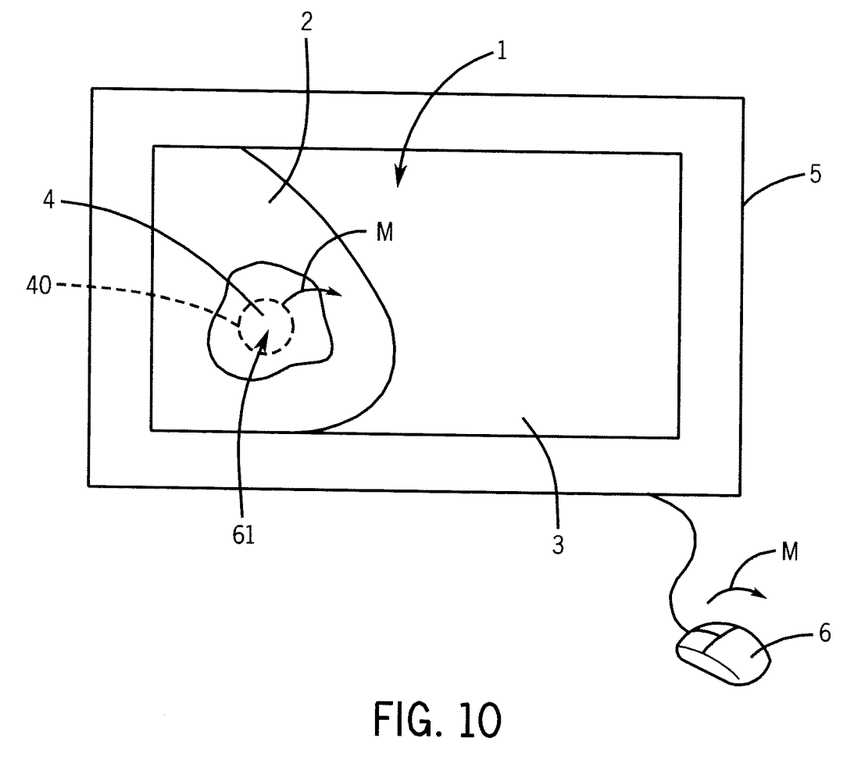
FIG. 10 is a schematic representation of a display of a digital mammogram.

FIG. 10 illustrates a schematic representation of a display of a digital mammogram. In FIG. 10, a display 5 is shown, which is arranged for example by a computer system with a screen and an input device 6. On the screen of the display 5 the mammogram 1 is represented, whereby by a selection of the input device 6 into the mammogram 1 the subsection 4 is defined. The place of a pointer 61 of the input device 6 in the mammogram 1 defines the center of subsection 4. Around the center of subsection 4 is a circular outline 40 of subsection 4. An increased contrast is stretched within the subsection 4 of mammogram 1. By moving the input device 6 for example in the direction of the arrow M, the pointer 61 on the display screen is moved and thus the subsection 4 within the mammogram 1 is shifted at the same time. In this way it may be more efficient for a user to locally optimize the contrast of a mammogram, so that the user may examine the internal structures within a mammogram in a simple manner.

While the disclosure has been described with reference to various embodiments, those skilled in the art will appreciate that certain substitutions, alterations and omissions may be made to the embodiments without departing from the spirit of the disclosure. In particular other outlines of which are possible subsections are possible, for example rectangular, square or elliptical outlines. Likewise the process of the weighting function can be varied and optimized over the subsection, in order to achieve a particularly pleasant and for a viewer favorable representation of the mammograms in the subsection and to avoid in particular artifacts in the boundary regions of the subsection. Accordingly, the foregoing description is meant to be exemplary only, and should not limit the scope of the disclosure as set forth in the following claims.

What is claimed is:

1. A method for displaying a digital mammographic image comprising:
   obtaining a mammographic image of an object, the mammographic image including a plurality of pixels with a pixel value assigned to each pixel;
   selecting a subsection within the mammographic image for optimizing the contrast of the subsection, wherein the pixel values of all pixels of the mammographic image are within a pre-determined first range of values and the pixel values of the pixels of a subsection are within a second range of values, wherein the second range of values represents a subset of the first range of values;
   optimizing the contrast of the subsection by applying a spreading function to the second range of values of the pixels within the subsection;
   decreasing contrast optimization towards a boundary of the subsection by applying a weighting function to the subsection; and
   displaying the mammographic image on a display with the contrast of the subsection spread in accordance with the spreading function.

2. The method of claim 1, wherein the second range of values of the pixels within the subsection are expanded by the spreading function to include the entire pre-determined first range of values.

3. The method of claim 1, wherein the subsection includes a substantially circular outline.

4. The method of claim 1, wherein the subsection of the mammographic image is definable by a user using an input device.

5. The method of claim 1, wherein a local position of the subsection in the mammographic image is changeable on a display by using an input device coupled to the display.

6. The method of claim 1 wherein the amount of the weighting function decreases near the boundary of the subsection.

7. An apparatus for displaying a digital mammographic image comprising:
- means for obtaining a mammographic image of an object, the mammographic image including a plurality of pixels with a pixel value assigned to each pixel;
- means for selecting a subsection within the mammographic image for optimizing the contrast of the subsection, wherein the pixel values of all pixels of the mammographic image are within a pre-determined first range of values and the pixel values of the pixels of a subsection are within a second range of values, wherein the second range of values represents a subset of the first range of values;
- means for optimizing the contrast of the subsection by applying a spreading function to the second range of values of the pixels within the subsection;
- means for decreasing contrast optimization towards a boundary of the subsection by applying a weighting function to the subsection; and
- means for displaying the mammographic image on a display with the contrast of the subsection spread in accordance with the spreading function.

* * * * *